(12) United States Patent
Lee et al.

(10) Patent No.: US 9,645,141 B2
(45) Date of Patent: May 9, 2017

(54) METHOD FOR DIAGNOSING BIOMARKERS AND BIOMARKER DIAGNOSIS KIT

(71) Applicant: KOREA INSTITUTE OF SCIENCE AND TECHNOLOGY, Seoul (KR)

(72) Inventors: Kwan Hyi Lee, Seoul (KR); Ho Young Park, Seoul (KR); Yu Chan Kim, Goyang-si (KR); Hyun Kwang Seok, Seoul (KR); Seok Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/093,305

(22) Filed: Nov. 29, 2013

(65) Prior Publication Data

US 2014/0170767 A1   Jun. 19, 2014

(30) Foreign Application Priority Data

Nov. 30, 2012 (KR) ......................... 10-2012-0138352
Nov. 29, 2013 (KR) ......................... 10-2013-0147569

(51) Int. Cl.
*G01N 33/543* (2006.01)

(52) U.S. Cl.
CPC .............................. *G01N 33/54326* (2013.01)

(58) Field of Classification Search
CPC .............................................. G01N 33/54326
See application file for complete search history.

(56) References Cited

U.S. PATENT DOCUMENTS

| | | | |
|---|---|---|---|
| 2008/0135490 A1* | 6/2008 | Li et al. | 210/695 |
| 2009/0258371 A1* | 10/2009 | Wardlaw et al. | 435/7.1 |
| 2010/0092384 A1* | 4/2010 | Bumb et al. | 424/1.29 |
| 2011/0003392 A1 | 1/2011 | Stayton et al. | |
| 2011/0244484 A1 | 10/2011 | Chae et al. | |

FOREIGN PATENT DOCUMENTS

| | | |
|---|---|---|
| JP | 2010-256116 A | 11/2010 |
| KR | 1020100126928 A | 3/2010 |
| KR | 1020110112177 A | 10/2011 |

OTHER PUBLICATIONS

Gao et al., In vivo molecular and cellular imaging with quantum dots, Current Opinion in Biotechnology 2005, 16:63-72.*
Gu et al., Biofunctional magnetic nanoparticles for protein separation and pathogen detection, Chem. Commun., 2006, 941-949.*
Fang et al., Superparamagnetic core-shell polymer particles for efficient purification of his-tagged proteins, J. Mater. Chem., 2010, 20, 8624-8630.*
Zrazhevskiy et al., Multicolor Quantum Dots in Molecular Profiling of Cancer Cells and Tissues, Encyclopedia of Inorganic Chemistry in 2009 by John Wiley & Sons, Ltd., pp. 1-16.*
Johnson et al., Engineered Protein A for the Orientation Control of Immobilized Proteins, Bioconjugate Chem. 2003, 14, 974-978.*
Lee et al., Quantitative molecular profiling of biomarkers for pancreatic cancer with functionalized quantum dots, Nanomedicine: Nanotechnology, Biology, and Medicine, 8 (2012) 1043-1051 (available online Jan. 31, 2012) pp. 1-27 on the HTML version.*
Xiaoshan Zhu at ai., Magnetic bead based assay for C-reactive using quantum-dot fluorescence labeling and immunoaffinity separation, Analyst, 2010, pp. 381-389, vol. 135,The Royal Society of Chemistry.
Chien-Sheng Chen at al, Protein G-liposomal nanovesicles as universal reagents for ummunoassays, Talanta, Mar. 17, 2005, pp. 205-21 , vol. 67, Elsevier.
Pan K. Bae et al. The modification of quantum dot probes used for the targeted imaging of his-tagged fusion proteins, Biomaterials, Dec. 10, 2009, pp. 838-842 , vol. 30, Elsevier.

* cited by examiner

*Primary Examiner* — Andrea S Grossman
(74) *Attorney, Agent, or Firm* — Goldilocks Zone IP Law

(57) ABSTRACT

A method for diagnosing a biomarker using magnetic particles and quantum dots for quantitative analysis and a biomarker diagnosis kit are provided. The method for diagnosing a biomarker includes: ii) providing magnetic particles having surfaces to which a primary antibody capable of collecting a biomarker using a linker is fixed; ii) providing quantum dots having surfaces to which a secondary antibody capable of detecting the biomarker is fixed; iii) sandwich-targeting the biomarker by the magnetic particles and the quantum dots; iv) selectively separating quantum dots sandwich-targeting the biomarker among the quantum dots; and v) quantifying the concentration of the biomarker by measuring absorbance or intensity of fluorescence of separated quantum dots.

4 Claims, 19 Drawing Sheets
(12 of 19 Drawing Sheet(s) Filed in Color)

METHOD FOR DIAGNOSING BIOMARKERS AND BIOMARKER DIAGNOSIS KIT

BACKGROUND OF THE INVENTION (a) Field of the Invention

The present invention relates to a method for diagnosing a biomarker and a biomarker diagnosis kit. More particularly, the present invention relates to a method for diagnosing a biomarker using a magnetic particle and a quantum dot for quantitative analysis, and a biomarker diagnosis kit.

(b) Description of the Related Art

Diagnosis kits that may diagnose a disease by detecting a single material or a plurality of materials from a sample such as urine or blood have been developed. In general, a biological receptor having a function of recognizing a specific material is coupled with an electrical or optical converter, and selectively detects a material to be analyzed by converting biological interactions and recognition reactions into electrical or optical signals.

Recently, diagnosis kits have been developed that give accurate and valuable information by accurately quantifying the amount of biomarker rather than a conventional qualitative analysis which simply judges whether there is a disease biomarker. Particularly, the quantification of a biomarker at a trace amount level leads to diagnosis and prediction even at the initial stage of a lethal disease such as cancer, and thus is highlighted as a future medical technology. Especially, new diagnosis methods have been developed while various nano-technologies are developing, and thus have been greatly highlighted.

SUMMARY OF THE INVENTION

A method that may quantitatively and accurately diagnose a biomarker using a magnetic particle and a quantum dot is provided. Further, a biomarker diagnosis kit that may quantitatively and accurately diagnose the above-described biomarker is provided.

An exemplary embodiment of the present invention provides a method for diagnosing a biomarker, including: i) providing magnetic particles having surfaces to which a primary antibody capable of collecting a biomarker using a linker is fixed; ii) providing quantum dots having surfaces to which a secondary antibody capable of detecting the biomarker is fixed; iii) sandwich-targeting the biomarker by the magnetic particles and the quantum dots; iv) selectively separating quantum dots sandwich-targeting the biomarker among the quantum dots; and v) quantifying the concentration of the biomarker by measuring absorbance or intensity of fluorescence of separated quantum dots.

The providing of the magnetic particles may include: i) functioning the surfaces of magnetic particles with a thiol; ii) binding at least one linker protein selected from the group consisting of protein G, protein A, protein NG, and an Fc receptor to surfaces of the magnetic particles using a chemical linker; and iii) activating the $F_{ab}$ of a primary antibody by fixing the primary antibody to the surface of the magnetic particles. In the binding of the linker protein, the chemical linker may be at least one chemical linker selected from the group consisting of sulfosuccinimidyl-4-{N-maleimidomethyl}cyclohexane-1-carboxylate and succinimidyl-4-{N-maleimidomethyl}cyclohexane-1-carboxylate (SMCC).

The providing of quantum dots may include: i) converting the surfaces of quantum dots to be hydrophilic by using at least one lipid selected from the group consisting of 1-myristoyl-2-hydroxy-sn-glycero-3-phosphocholine (MHPC), 1,2-distearoyl-sn-glycero-3-phosphoethanolamine-N-(methoxy polyethylene glycol-2000) (DPPE-PEG2000), and 1,2-dioleoyl-sn-glycero-3-N-{5-amino-1-carboxypentyl}iminodiacetic acid succinyl nickel salt (Ni-NTA); ii) fixing a linker protein including a hexahistidine sequence to the surface of quantum dot using a nickel-histidine binding reaction; and iii) fixing a secondary antibody on the linker protein. In the fixing of the linker protein, the linker protein may be at least one protein selected from the group consisting of protein G, protein A, protein A/G, and an Fc receptor, and the $F_{ab}$ of the secondary antibody may be constantly activated by the linker protein. The selectively separating of quantum dots sandwich-targeting the biomarker may include: i) separating only quantum dots attached to the secondary antibody by adding at least one additive selected from the group consisting of imidazole and ethylenediamine tetraacetic acid (EDTA) to break the nickel-histidine binding reaction; and ii) removing magnetic particles by using magnetic force.

The quantifying of the concentration of the biomarker may include: i) providing a plurality of solutions including other quantum dots which are different in concentration; ii) measuring the absorbance or intensity of fluorescence of the plurality of solutions at a wavelength of 350 nm; iii) providing a standard curve by comparing the concentration and the absorbance or the intensity of fluorescence of the other quantum dots; iv) measuring the absorbance or intensity of fluorescence of the separated quantum dot at a wavelength of 350 nm; v) calculating the concentration of the separated quantum dot by comparing the absorbance or intensity of fluorescence of the separated quantum dot at a wavelength of 350 nm with the standard curve; and vi) quantifying the concentration of the biomarker proportional to the concentration of the separated quantum dot.

In the providing of magnetic particles, the primary antibody may consist of a plurality of antibodies, and in the providing of quantum dots, the secondary antibody may consist of a plurality of antibodies. In the sandwich-targeting of the biomarker, the biomarker may consist of a plurality of biomarkers, the plurality of biomarkers may be different from each other, and the primary antibody and the secondary antibody for each of the biomarkers may be different from each other. In the providing of quantum dots, the quantum dots may include a material composed of a core/shell of CdSe/ZnS.

Another exemplary embodiment of the present invention provides a biomarker diagnosis kit including: i) a first container containing a magnetic particle-containing solution for collecting a biomarker; ii) at least one second container separate from the first container and containing a quantum dot-containing solution for quantitative analysis; iii) a third container separate from the second container and containing a buffer solution which includes at least one separating agent selected from the group consisting of imidazole and ethylenediamine tetraacetic acid (EDTA); iv) a fourth container separate from the third container and being hollow; v) a magnetic body separate from the first container to the fourth container; and vi) a description document separate from the first to fourth containers and the magnetic body.

The description document may direct a content including: i) providing a first mixed solution by placing a biomarker and a solution from the first container into a the fourth container; ii) leaving only an object attached to a magnetic body in the first mixed solution by bringing the magnetic body in contact with the fourth container; iii) providing a second mixed solution by placing the solution from the second container into the fourth container; iv) providing a third mixed solution in which the second mixed solution and the solution from the third container are mixed by placing the solution from the third container into the fourth container; and v) separating the remnant solution except for magnetic particles attached to the magnetic body in the third mixed solution by bringing the magnetic body in contact with the fourth container. The description document may additionally direct a content including: i) measuring absorbance or intensity of fluorescence of the remnant solution; ii) providing a standard curve which compares the concentration and the absorbance or intensity of fluorescence of a biomarker; iii) calculating the concentration of the remnant solution by comparing the absorbance or intensity of fluorescence with the standard curve; and iv) quantifying the concentration of the biomarker proportional to the concentration of the remnant solution. At least one second container includes a plurality of second containers, and different quantum dot-containing solutions for quantitative analysis may be included in each of the plurality of second containers.

The concentration of the biomarker may be accurately quantified by combining the magnetic particles with the quantum dots. As a result, accurate information on disease may be obtained from the biomarker. It is therefore possible for clinicians in hospitals to diagnose a disease, judge a prognosis for a drug or therapy, and perform a medical check-up. Further, various diseases may be easily predicted from a commercially available biomarker diagnosis kit. In addition, a trace of various proteins and biomarkers may be quantitatively analyzed. Moreover, since a plurality of biomarkers may be simultaneously and quantitatively analyzed, the accuracy of disease diagnosis may be enhanced as compared to the case of using only one biomarker. Further, since multiple analysis is performed using a plurality of biomarkers, the examination time and the examination cost may be reduced.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
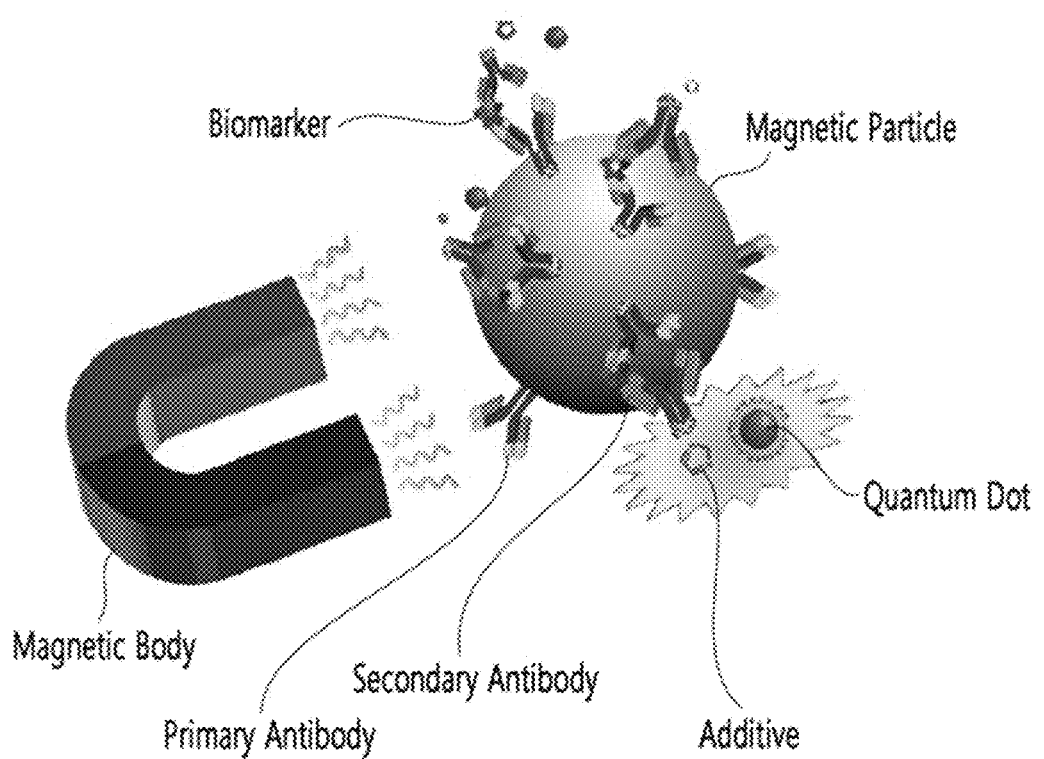
FIG. 1 is a schematic concept view of a method for diagnosing a biomarker according to a first exemplary embodiment of the present invention.

In the following detailed description, when it is stated that one part is "on" another part, one part may be directly on another part or yet another part may be interposed therebetween. To the contrary, when it is stated that one part is "directly on" another part, another part is not interposed therebetween.

The terms "first", "second", and "third" are used to explain various parts, components, regions, layers and/or sections, but it should be understood that they are not limited thereto. These terms are used only to discriminate one part, component, region, layer, or section from another part, component, region, layer, or section. Thus, a first part, component, region, layer, or section described below may be referred to as a second portion, component, region, layer, or section within a range not departing from the scope of the present invention.

The technical terms used herein are to simply mention a particular embodiment, and are not intended to limit the present invention. An expression used herein in the singular form encompasses the expression of the plural form, unless a clearly opposite meaning is indicated in the context. The meaning of "including" used in the specification implements specific features, regions, integers, steps, actions, elements, and/or components, and is not intended to preclude the presence or addition of other features, regions, integers, steps, actions, elements, and/or components.

Terms indicating relative spaces such as "below" and "above" may be used to more easily describe the relationships of one part with another part illustrated in the drawings. Such terms are intended to include different meanings or operations of a device in use along with meanings intended by the drawings. For example, if a device in a drawing is reversed, one part described to be "under" or "below" the other part is described to be "on" or "above" the other part. Thus, terms illustrative of "under" or "below" may include all the downward and upward directions. A device may be rotated by 90° or other angles, and terms representing a relative space may be interpreted accordingly.

Unless otherwise defined, all terms used herein, including technical or scientific terms, have the same meanings as those generally understood by those skilled in the art to which the present invention pertains. Such terms defined in a generally used dictionary are not to be interpreted to have idealized or excessively formal meanings unless additionally interpreted and clearly defined to have meanings which match the related technical literatures and the contents currently disclosed.

The term "biomarker" used below refers to an index that may detect the change of a body caused by effects of genetic or epigenetic changes in an organism as molecular information based on the pattern of a single molecule or molecules derived from DNA, RNA, metabolites, proteins, and protein pieces. Thus, it is interpreted that a biomarker is included in blood, serum, or urine which is a material to be measured, and the diagnosis of the biomarker is interpreted to be a diagnosis of a sample such as blood, serum, or urine.

The term "magnetic particle" used below includes an object composed of a single particle or a plurality of particles having a size from 1 nm to 10 μm. In this case, the magnetic particle is interpreted to include all of metal materials, magnetic materials, and magnetic alloys.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

FIG. 1 schematically and conceptually illustrates a method for diagnosing a biomarker according to a first exemplary embodiment of the present invention. The concept of a method for diagnosing a biomarker in FIG. 1 is provided only for illustrating the present invention, and the present invention is not limited thereto. Therefore, the concept of a method for diagnosing a biomarker may be modified into another form.

As illustrated in FIG. 1, a first exemplary embodiment of the present invention provides a magnetic particle having a surface to which a primary antibody is fixed and a quantum dot having a surface to which a secondary antibody is fixed. A biomarker may be collected by a first antibody, and detected by a second antibody. The biomarker collected by the first antibody is separated by a magnetic body, and then detected by a secondary antibody bound to a quantum dot. Thus, the biomarker is sandwich-targeted by the magnetic particle and the quantum dot. Next, the targeted biomarker may be selectively separated by an additive while the biomarker is attached to the magnetic particle. As a result, the concentration of the biomarker may be quantified through a quantum dot. Hereinafter, the concept of the method for diagnosing a biomarker of FIG. 1 will be described in more detail through FIGS. 2 to 8.

Figure 2:
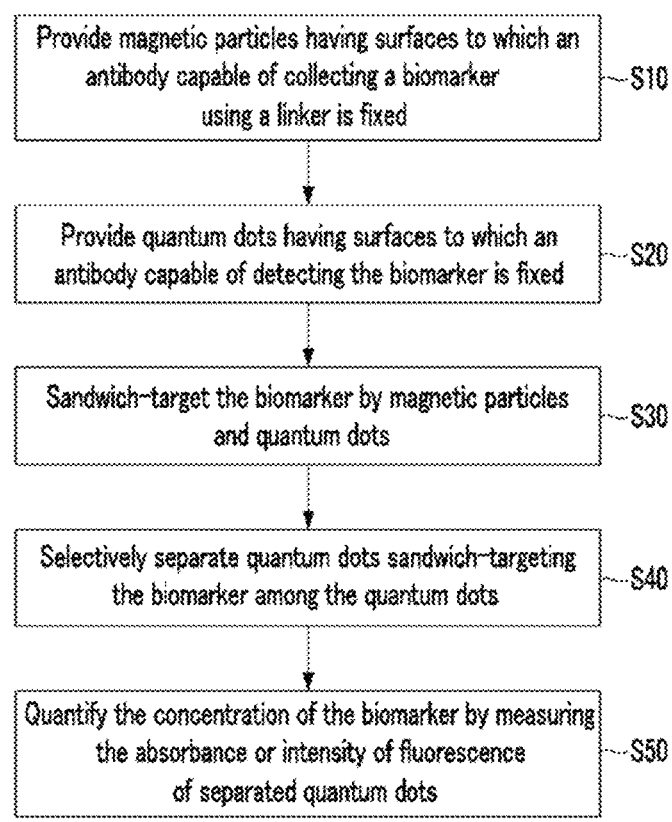
FIG. 2 is a schematic flowchart of a method for diagnosing a biomarker according to a first exemplary embodiment of the present invention.

FIG. 2 schematically illustrates a flowchart of a method for diagnosing a biomarker according to a first exemplary embodiment of the present invention. The method for diagnosing a biomarker of FIG. 2 is provided only for illustrating the present invention, and the present invention is not limited thereto. Thus, the method for diagnosing a biomarker may be variously modified. Hereinafter, the method for diagnosing a biomarker will be described in detail with reference to FIGS. 3 to 8 which conceptually illustrate each step of the method for diagnosing a biomarker of FIG. 2.

As illustrated in FIG. 2, the method for diagnosing a biomarker includes providing magnetic particles having surfaces to which an antibody capable of collecting a biomarker using a linker is fixed (S10), providing quantum dots having surfaces to which an antibody capable of detecting the biomarker is fixed (S20), sandwich-targeting the biomarker by the magnetic particles and the quantum dots (S30), selectively separating quantum dots sandwich-targeting the biomarker among the quantum dots (S40), and quantifying the concentration of the biomarker by measuring the absorbance or intensity of fluorescence of separated quantum dots (S50). The method for diagnosing a biomarker may further include other steps if necessary.

First, step S10 of FIG. 2 provides magnetic particles having surfaces to which an antibody capable of collecting a biomarker using a linker is fixed. In connection with this, FIG. 3 conceptually illustrates a method for preparing a magnetic particle for collecting a biomarker by fixing an antibody capable of collecting the biomarker to the surface of the magnetic particle using a linker.

Figure 3:
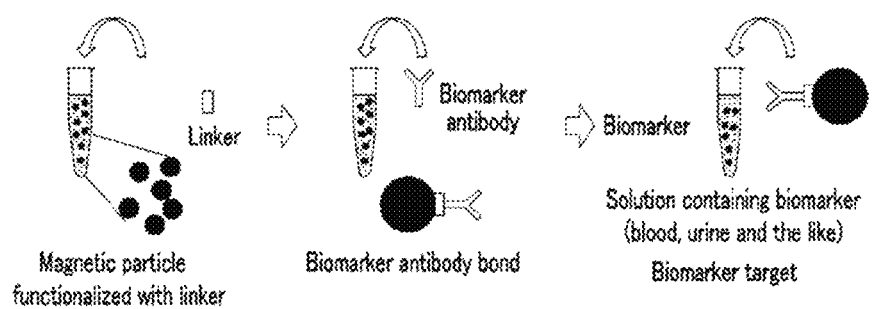
FIG. 3 to FIG. 8 are views conceptually illustrating each step of the method for diagnosing a biomarker of FIG. 1.

As illustrated in FIG. 3, protein G, protein A, protein A/G, or an Fc receptor, which is a linker which binds an antibody that detects a biomarker to a magnetic particle, is specifically bound to an Fc moiety of the antibody. Thus, an $F_{ab}$ moiety of an antibody for collecting a biomarker may be constantly activated. Since the $F_{ab}$ moiety of an antibody is bound to a magnetic particle while the $F_{ab}$ moiety is constantly activated, the magnetic particle may be well functionalized. The surface of the magnetic particle may also be functionalized with a thiol. Particularly, since it is highly likely that the $F_{ab}$ moiety of the antibody may not be activated from the non-specific bonding of, for example, N-hydroxysuccinimide (hereinafter referred to as "NHS")-ethyl(dimethylaminopropyl)carbodiimide (hereinafter referred to as "EDC") antibody to nanoparticles, the general chemical bonding method ultimately deteriorates the target efficiency. Thus, it is necessary to perform a reaction with an excessive amount of expensive antibodies in order to overcome the low efficiency. To the contrary, since protein G, protein A, protein A/G, or an Fc receptor is utilized as a linker protein in step S10 of the method for diagnosing a biomarker according to the first exemplary embodiment of the present invention, the linker is specifically bound to the Fc moiety of the antibody, and the $F_{ab}$ moiety of the antibody is constantly activated. As a result, the ability of the biomarker to collect the antibody may be maximized.

A chemical linker may be used in order to bind the linker protein to the surfaces of magnetic particles. As the chemical linker, sulfosuccinimidyl-4-{N-maleimidomethyl}cyclohexane-1-carboxylate or succinimidyl-4-{N-maleimidomethyl}cyclohexane-1-carboxylate (SMCC) may be used. As a result, the efficiency of targeting the biomarker may be increased. That is, the antibody may be fixed to the surface of magnetic particles by putting magnetic particles into a solution containing a biomarker such as blood, serum, or urine. The antibody is fixed to the surface of the magnetic particles to activate the $F_{ab}$ of the antibody.

Next, step S20 of FIG. 2 provides quantum dots having surfaces to which a secondary antibody capable of detecting the biomarker is fixed. In connection with this, FIG. 4 conceptually illustrates a state of preparing a quantum dot for quantitative analysis by fixing the antibody capable of detecting the biomarker to the surface of the quantum dot.

Figure 4:
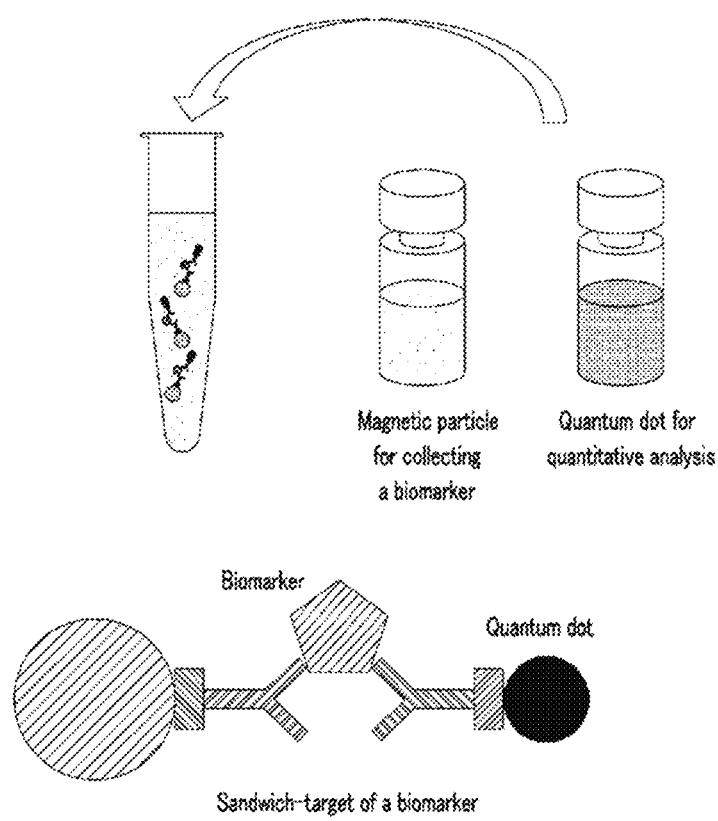
Figure 5:
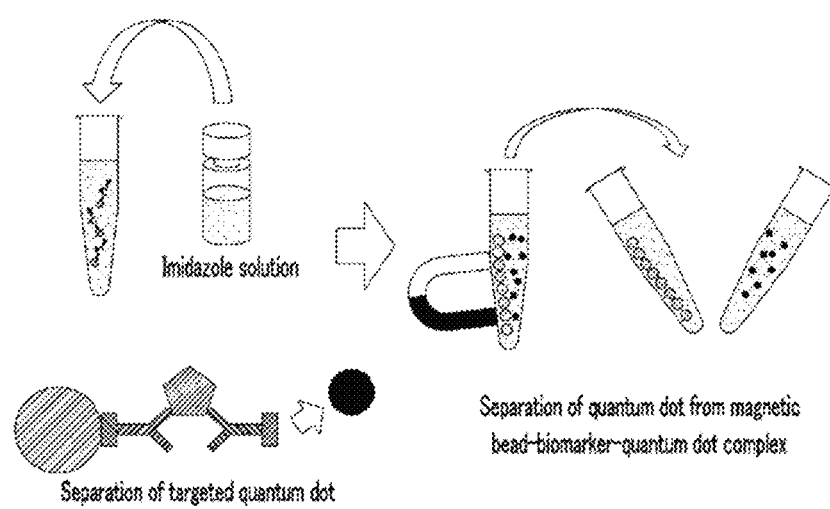
Figure 6:
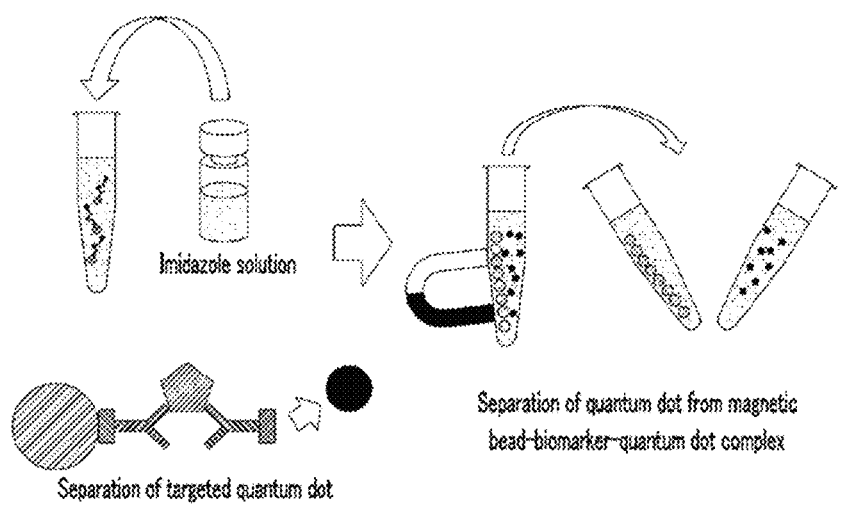

As illustrated in the lower portion of FIG. 4, the histidine sequence of protein G bound to the Fc moiety of an antibody for detecting a biomarker is reacted with an Ni-NTA in the lipid layer of the surface of the quantum dot in order to form a complex composed of an antibody for detecting a biomarker-protein G (linker)-quantum dot. That is, the antibody for detecting a biomarker is fixed to the surface of a hydrophilic quantum dot prepared by binding the antibody to protein G including a histidine sequence and using a lipid including the Ni-NTA. The quantum dot needs to minimally generate an aggregation phenomenon while having hydrophilic properties, and needs to be functionalized with nickel. When a hydrophilic lipid layer is produced on the surface of the quantum dot in order to satisfy the above-described required conditions, the lipid layer is optimized while having inherent components and inherent component ratios.

The lipid layer of the surface of the quantum dot is composed of three types of lipids. That is, the lipid layer of the surface of the quantum dot is composed of 1-myristoyl-2-hydroxy-sn-glycero-3-phosphocholine (hereinafter referred to as "MHPC"), 1,2-distearoyl-sn-glycero-3-phosphoethanolamine-N-(methoxy polyethylene glycol)-2000 (hereinafter referred to as "DPPE-PEG2000"), and 1,2-dioleoyl-sn-glycero-3-N-{5-amino-1-carboxypentyl}iminodiacetic acid succinyl nickel salt (hereinafter referred to as "Ni-NTA"). An emulsion state is prepared by sequentially mixing predetermined amounts of MHPC, DPPE-PEG2000, and Ni-NTA with quantum dots, and a functional lipid layer is formed on the surface of the quantum dots by treatment with ultrasonic waves. In this case, the hydrophobic moiety of the lipid is bound to the surface of the quantum dot by a hydrophobic bond, and thus may coat the surface of the quantum dot while the hydrophilic moiety of the lipid is externally oriented, thereby converting the surface of the quantum dot to be hydrophilic.

The MHPC is a single acyl group-chained lipid, and thus may densely coat the spherical surface. In addition, DPPE-PEG2000 imparts stability to a quantum dot coated with a lipid. Furthermore, Ni-NTA is bound to histidine in protein G to bind the hydrophilic quantum dot to protein G, and serves to selectively separate the hydrophilic quantum dot and protein G when an imidazole is added thereto in the subsequent process for separation of quantum dots.

A linker protein including a hexahistidine sequence is fixed to the surface of the quantum dot by using a nickel-histidine binding reaction, and a secondary antibody is fixed on the linker protein. Herein, protein G, protein A, protein A/G, or an Fc receptor may be used as the linker protein, and the $F_{ab}$ of the antibody is constantly activated by the linker protein. As a result, a functionalized quantum dot-nanostructure capable of quantifying a biomarker may be prepared by adding a hydrophilic quantum dot to a conjugate of an antibody for detecting a biomarker and protein G.

Meanwhile, in step S30 of FIG. 2, a biomarker is sandwich-targeted by magnetic particles and quantum dots. In connection with this, FIG. 5 conceptually illustrates the state where the biomarker is sandwich-targeted by using a magnetic particle as a nanostructure and a quantum dot. That is, the biomarker is present while being targeted both by the magnetic particle and the quantum dot. Thus, a biomarker may be quantified by using the magnetic particle and the quantum dot in a subsequent process.

Next, in step S40 of FIG. 2, the quantum dots sandwich-targeting the biomarker are selectively separated among quantum dots. In connection with this, FIG. 6 conceptually illustrates the state where only the quantum dot targeting the biomarker is selectively separated.

That is, it is possible to use an excessive amount of imidazole having a similar structure to that of histidine as an additive. EDTA may be used instead of imidazole. Quantum dots attached to the antibody are separated by adding imidazole or EDTA thereto to break a bond between histidine of protein G used as a linker and Ni-NTA on the surface of the quantum dot, that is, a nickel-histidine binding reaction. The separated quantum dot maintains inherent optical properties as it is. Thus, magnetic particles are left to reside in a solution and removed by magnetic force using a magnetic body such as a magnet, and only the quantum dot may be distinctly separated. Moreover, the concentration of the biomarker may be quantified by using the absorbance or intensity of fluorescence that the separated quantum dot indicates.

Figure 7:
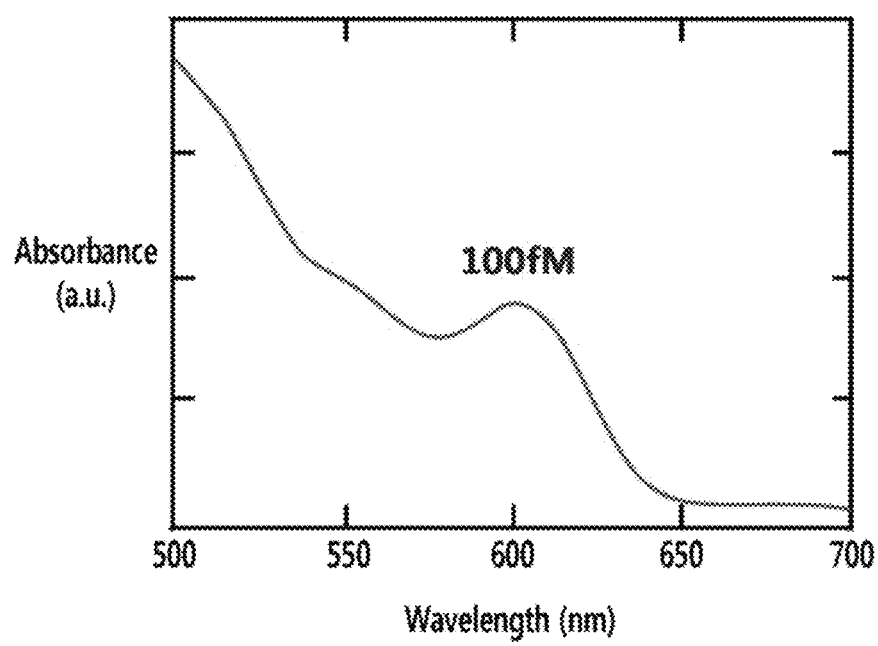

Finally, in step S50 of FIG. 2, the concentration of the biomarker is quantified by measuring the absorbance of separated quantum dots. The intensity of fluorescence, that is, the intensity of emission, may be measured instead of the absorbance. In connection with this, FIG. 7 illustrates a graph in which the concentration of the biomarker is quantified by measuring the absorbance of the separated quantum dot. As illustrated in FIG. 7, the concentration of the biomarker may be accurately measured by measuring the absorbance using the quantum dot. Thus, it is possible to accurately diagnose the biomarker. For example, in order to provide a standard curve, a plurality of solutions including hydrophilic quantum dots that are different from each other in concentration are provided, and the absorbance thereof is measured at a wavelength of 350 nm. Thus, a standard curve may be provided by comparing the concentration of quantum dots with the absorbance. The concentration of the quantum dots may be calculated by using optical characteristics of a selectively separated quantum dot solution through measurement of the absorbance at 350 nm using a standard curve, and the concentration of the biomarker proportional to the concentration of the quantum dot may be quantitatively analyzed.

Due to a magnetic phenomenon of magnetic particles or a phenomenon in which the intensity of fluorescence of the quantum dot is drastically weakened when the magnetic particle is close to the quantum dot in the related art, it is difficult to perform a quantitative analysis of the biomarker. For example, when the prostate-specific antigen (PSA) is separated, detected, and quantified using the magnetic particle, a change in electrical conductivity caused by cadmium ions constituting the quantum dot was measured by dissolving the quantum dot in a strong acid. However, there was a problem in that a large amount of cadmium ions are generated, thereby being detrimental to the human body. Further, in order to measure the inherent fluorescence by separating the quantum dot from the magnetic particle, an alkali solution and an organic solvent at high concentrations were used in order to break the streptavidin-biotin bond, but quantum dots could be aggregated by the organic solvent. In addition, since the stability and optical characteristics of the quantum dot deteriorate, a test was needed to be performed by preparing various buffer solutions, and there was a problem in that reproducibility deteriorated.

To the contrary, in an exemplary embodiment of the present invention, the quantum dot targeting the biomarker is simply separated from the magnetic particle while maintaining the inherent optical characteristics. Furthermore, the biomarker may be accurately and quantitatively analyzed by making the concentration of the quantum dot proportional to the concentration of the biomarker such that the quantum dots are not aggregated. That is, in the first exemplary embodiment of the present invention, the biomarker is sandwich-targeted by using only the magnetic particles and the quantum dots without using a special apparatus, and then only the targeted quantum dot is selectively and easily separated without affecting optical characteristics of the quantum dot using the imidazole. As a result, the number of biomarkers may be quantitatively analyzed with high sensitivity by excluding the influence of other materials and using the absorbance as one of the inherent physical properties of the quantum dot.

Figure 8:
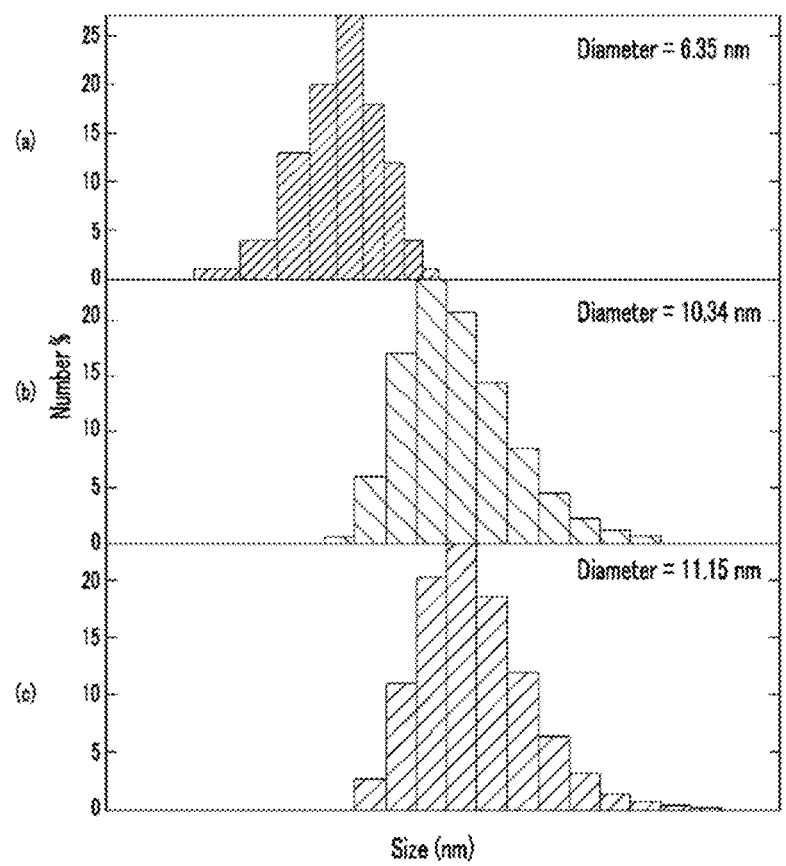

FIG. 8 illustrates a graph showing that the change in size of the quantum dot according to the functionalization of the quantum dot is measured by dynamic light scattering (hereinafter referred to as "DLS"). FIG. 8 (a) illustrates the measurement of the size of the quantum dot in the organic solvent, FIG. 8 (b) illustrates the measurement of the size of the quantum dot to be hydrophilically prepared, and FIG. 8 (c) illustrates the size measured after the hydrophilic quantum dot is bound to the antibody.

FIG. 8 conceptually illustrates the principle that the concentration of the biomarker is quantified by using the absorbance of the quantum dot, and in FIG. 8, it can be seen that the size of the quantum dot is gradually increased as the quantum dot becomes hydrophilic and the antibody is bound to the quantum dot. That is, as illustrated in FIG. 8 (a) to FIG. 8 (c), the diameter of the quantum dot is gradually increased from 6.35 nm→10.34→nm 11.15 nm. Thus, it is possible to know the process of preparing a hydrophilic quantum dot through the DLS measurement value and that the antibody for detecting a biomarker is well bound to the hydrophilic quantum dot.

Figure 9:
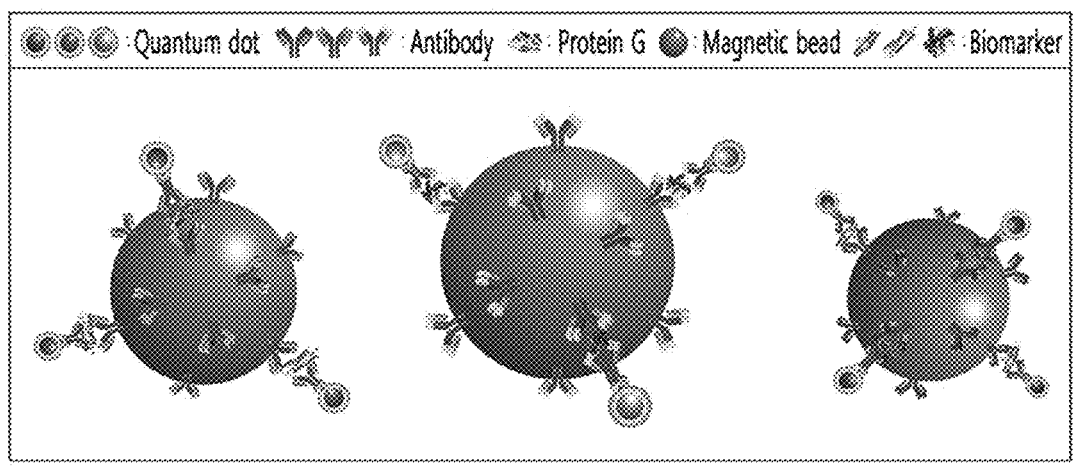
FIG. 9 is a schematic concept view of a method for diagnosing a biomarker according to a secondary exemplary embodiment of the present invention.

FIG. 9 schematically and conceptually illustrates a method for diagnosing a biomarker according to the secondary exemplary embodiment of the present invention. The concept of the method for diagnosing a biomarker of FIG. 9 only illustrates the present invention, and the present invention is not limited thereto. Thus, the concept of the method for diagnosing a biomarker may be modified into another form. Further, since the method for diagnosing a biomarker according to the second exemplary embodiment of the present invention in FIG. 9 is similar to the method for diagnosing a biomarker according to the first exemplary embodiment of the present invention of FIG. 1, the detailed description of the same contents will be omitted.

As illustrated in FIG. 9, a quantitative analysis is performed by simultaneously detecting multiple biomarkers. That is, the primary antibody is bound to the functionalized magnetic particle by putting the primary antibody into the functionalized magnetic particle and the primary antibody different from the above-described primary antibody is bound to the functionalized magnetic particle by using the same amount of the functionalized magnetic particles. A mixed solution of a primary antibody fixed magnetic particle group is prepared by mixing magnetic particle solutions to which primary antibodies different from each other are bound. That is, magnetic particles are divided into two or more groups, and are bound to primary antibodies targeting the biomarkers different from each other for each group.

Moreover, protein G is bound to the Fc moiety of the secondary antibody by reacting a protein G solution with the secondary antibody at room temperature. Protein G is also bound to a secondary antibody different from the above-described secondary antibody by the same method using the same amount of the protein G solution. In the meantime, the quantum dot which becomes hydrophilic by coating the lipid combination including nickel is added to the primary antibody fixed magnetic particle group mixed solution that is previously prepared, and then the resulting mixture is reacted at room temperature. In this case, the emission wavelength of the quantum dot is selected from the group consisting of approximately 520 nm, 620 nm, and 710 nm. The quantum dot includes a material composed of a core/shell of CdSe/ZnS.

Figure 10:
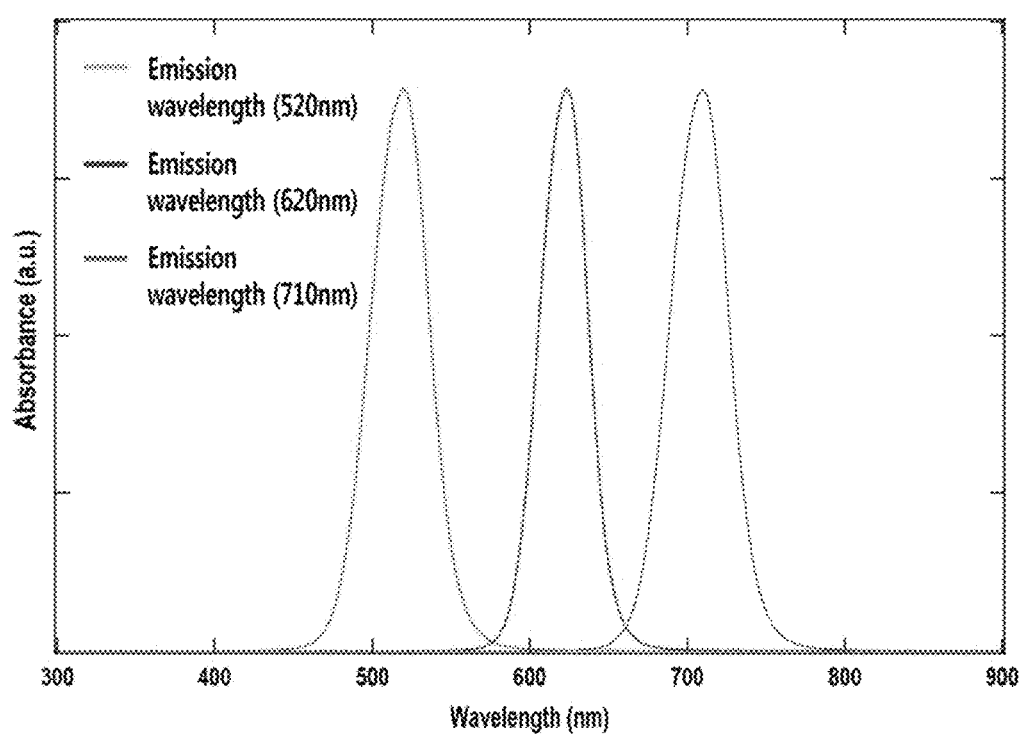
FIG. 10 is a graph showing fluorescent characteristics of different quantum dots.

FIG. 10 schematically illustrates fluorescent characteristics of quantum dots that are different from each other. As illustrated in FIG. 10, the emission wavelengths of the quantum dots are each selected from the group consisting of 520 nm, 620 nm, and 710 nm, and are different from each other. Through the above-described method, each of the secondary antibodies targeting the biomarkers that are different from each other is fixed to each of the quantum dots exhibiting fluorescent characteristics that are different from each other, selected from the hydrophilic quantum dot group.

Moreover, a biomarker is targeted by putting biomarkers that are different from each other and a phosphate buffer solution into a mixed solution of a group of three magnetic particles in which primary antibodies that are different from each other are fixed and reacting the mixture at room temperature. In this case, the antibody to be used is an antibody which selectively reacts with pancreatic cancer biomarkers that are different from each other. The secondary antibodies are bound to hydrophilic quantum dots emitting fluorescence of different colors. That is, each of the secondary antibodies targeting biomarkers that are different from each other is fixed to each of the quantum dots exhibiting fluorescent characteristics that are different from each other selected from the hydrophilic quantum group.

Next, the biomarker is sandwich-targeted by sequentially putting secondary antibodies that are different from each other into a solution in which the primary antibody is targeted by the magnetic particle group mixed solution. The secondary antibody used in this case is selectively reacted with pancreatic cancer biomarkers that are different from each other, and a quantum dot emitting fluorescence of different colors is bound to each antibody. The secondary antibody to which an excessive amount of quantum dots is bound is washed with a phosphate buffer solution and completely removed.

A standard curve is prepared by using a result of measuring a fluorescent intensity value for each concentration by using quantum dots at different concentrations. A standard curve may be provided by comparing the intensity of fluorescence of a plurality of solutions including quantum dots at different concentrations for quantum dots exhibiting fluorescent characteristics that are different from each other from the hydrophilic quantum dot group.

Further, different quantum dots bound to the secondary antibody are separated by adding an imidazole solution to a sandwich assay and reacting the resulting mixture at room temperature. Each of different quantum dots corresponding to the number of molecules of the biomarker and selectively separated is obtained by attracting magnetic particles using a magnet, and then collecting a supernatant. In addition, the fluorescent intensity value is measured by setting the solution obtained so as to have emission wavelengths of 520 nm, 620 nm, and 710 nm. That is, the concentration is calculated by comparing the intensity of fluorescence of each quantum dot separated for quantifying the concentration of multiple biomarkers with the standard curve, and the concentration of the biomarker proportional to the concentration of each separated quantum dot is quantified. Thus, a quantitative analysis may be performed by knowing the concentration of each separated biomarker.

Figure 11:
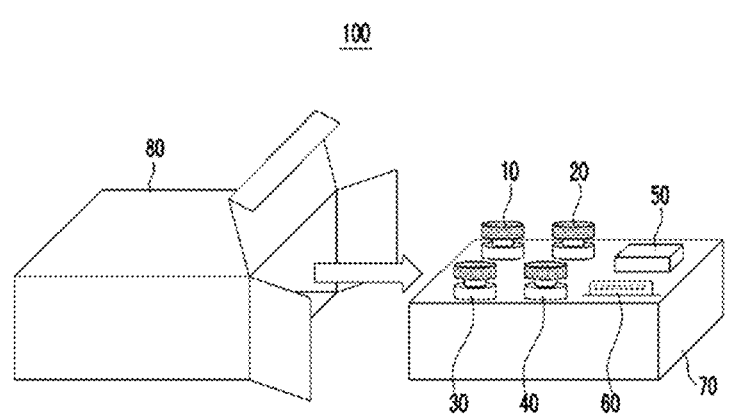
FIG. 11 is a schematic view of a biomarker diagnosis kit according to an exemplary embodiment of the present invention.

FIG. 11 schematically illustrates a biomarker diagnosis kit 100 according to an exemplary embodiment of the present invention. The structure of the biomarker diagnosis kit 100 of FIG. 11 is provided only for illustrating the present invention, and the present invention is not limited thereto. Thus, the structure of the biomarker diagnosis kit 100 may be modified into another form.

As illustrated in FIG. 11, the biomarker diagnosis kit 100 includes first to fourth containers 10, 20, 30, and 40, a magnetic body 50, a description document 60, a fixing stand 70, and a case 80. The biomarker diagnosis kit 100 may further include other parts, if necessary. The first to fourth containers 10, 20, 30, and 40, the magnetic body 50, and the description document 60 are positioned while being fixed to the fixing stand 70, and may be used while being pulled out in an arrow direction from the case 80. Unlike those illustrated as in FIG. 9, the description document 60 may be included in the case 80 independently of the fixing stand 70 without being placed into the fixing stand 70.

A solution including magnetic particles for collecting a biomarker is received in the first container 10. The second container 20 is spaced apart from the first container 10 and is separately placed into the fixing stand 70. A solution including quantum dots for quantitative analysis is received in the second container 20. Unlike FIG. 16, the second container may be composed of a plurality of containers if necessary. In this case, each of the different solutions including quantum dots for quantitative analysis may be included in each of the plurality of second containers.

Further, the third container 30 is also separately placed into the fixing stand 70 while being spaced apart from the first container 10 and the second container 20. A buffer solution including imidazole is received in the third container 30. The fourth container 40 is separately placed into the fixing stand 70 while being spaced apart from the first container 10, the second container 20, and the third container 30. The fourth container 40 is hollow. Meanwhile, the magnetic body 50 is separately placed into the fixing stand 70 while being spaced apart from the first container 10, the second container 20, the third container 30, and the fourth container 40. A magnet may be used as the magnetic body 50. Moreover, the description document 60 is separately placed into the fixing stand 70 while being spaced apart from the first container 10, the second container 20, the third container 30, the fourth container 40, and the magnetic body 50.

Although not illustrated in FIG. 11, the description document 60 directs the content including i) providing a first mixed solution by placing a biomarker and a solution from the first container 10 into the fourth container 40, ii) leaving only an object attached to the magnetic body 50 in the first mixed solution by bringing the magnetic body 50 into contact with the fourth container 40, iii) providing a second mixed solution by placing the solution from the second container 20 into the fourth container 40, iv) providing a third mixed solution in which the second mixed solution and the solution from the third container 30 are mixed by placing the solution from the third container 30 into the fourth container 40, and v) separating the remnant solution except for magnetic particles attached to the magnetic body 50 in the third mixed solution by bringing the magnetic body 50 into contact with the fourth container 40. Thus, even a beginner may easily diagnose a biomarker according to the content of the description document 60.

The method for using a biomarker diagnosis kit 100 will be described in more detail as follows. First, a biomarker such as urine, serum, or blood and magnetic particles included in the first container 10 are mixed in the fourth container 40, and only the magnetic particles are left by using the magnetic body 50. Further, the biomarker is sandwich-targeted by the magnetic particle and the quantum dot by putting the quantum dot included in the secondary container 20 into the fourth container 40, and the quantum dot is separated from the biomarker by putting imidazole or EDTA from the third container 30 into the fourth container 40. In addition, only the quantum dot is separated by leaving only the magnetic particles to which the biomarker is fixed using the magnetic body 50 in the fourth container 40 and pouring the remnant solution into another container. Finally, the concentration of the quantum dot may be calculated from the separated solution according to a standard curve extracted by comparing the concentration and the absorbance or intensity of fluorescence of separated quantum dots, and the concentration of the biomarker may be quantified therefrom.

Meanwhile, the description document 60 may additionally direct the content including i) measuring the absorbance or intensity of fluorescence of the remnant solution, ii) providing a standard curve which compares the concentration and the absorbance or intensity of fluorescence of a biomarker, iii) calculating the concentration of the remnant solution by comparing the absorbance or intensity of fluorescence with the standard curve, and iv) quantifying the concentration of the biomarker that is proportional to the concentration of the remnant solution. Herein, the standard curve may be provided while being printed on the description document 60. Thus, the amount of the biomarker sandwich-targeting the quantum dot may be accurately calculated by comparing the absorbance of the remnant solution in which the quantum dot is included with the standard curve to obtain the amount of quantum dots included in the remnant solution. As a result, a diagnosis may be accurately performed according to the amount of the biomarker. The solution including quantum dots for quantitative analysis may include a quantum dot group for quantitative analysis composed of a plurality of biomarkers.

Hereinafter, the present invention will be described in more detail through experimental examples. The experimental examples are provided only for illustrating the present invention, and the present invention is not limited thereto. More specifically, a quantitative analysis experiment performed on the C-reactive protein will be described below. However, since the experimental examples are provided only for illustrating the present invention and the present invention is not limited thereto, different types of biomarkers may also be accurately and quantitatively analyzed by using the present invention.

Experimental Example 1

Functionalization of Magnetic Particles 9 mg of magnetic particles coated with a sulfhydryl group were washed with desalinated water. Then, the desalinated water was filtered three times by using a magnet. Next, a magnetic particle solution at a concentration of 30 mg/ml was prepared by re-floating the magnetic particles in 300 µl of desalinated water. The sulfhydryl group in the magnetic particles was converted into an activated state by putting 100 µl of β-mercapto ethanol at a concentration of 14.2 M into the magnetic particle solution and reacting the resulting mixture at room temperature for 30 minutes. By doing this, magnetic particles could be prevented from being aggregated together by breaking the bond with the sulfhydryl group of magnetic particles different from the sulfhydryl group on the surfaces of the magnetic particles. Further, in order to remove an excessive amount of β-mercapto ethanol, a solution having a final volume of 1 ml was prepared by washing the magnetic particles with a binding buffer solution composed of 5 mM of ethylenediamine tetraacetic acid (EDTA) having pH of 7.2, and adding a phosphate buffer solution having pH of 7.2 thereto. In addition, 5 µg/mL of a sulfo-SMCC solution was prepared such that a stable thioether bond with magnetic particles is formed, and the solution was reacted at room temperature for 30 minutes. Moreover, an excessive amount of the sulfo-SMCC solution was washed three times by using 1 ml of a phosphate buffer solution having pH of 7.2.

Antibody Fixation of Surface of Magnetic Particles

5 µl of a protein G solution at 1 µg/mL was put into functionalized magnetic particles, and the resulting mixture was reacted at room temperature for 1 hour. As a result, an NHS group in the sulfo-SMCC was bound to an amine group in protein G to form a stable amide bond. A supernatant was removed in order to prevent the non-specific binding of sulfhydryl groups remaining without being reacted. Further, 1 mL of cysteine at 8 µg/mL was added to magnetic particles, and the resulting mixture was reacted at room temperature for 30 minutes. In addition, in order to prevent a C-reactive protein antibody from being non-specifically bound to the surface of the remaining unreacted magnetic particles, 1 mL of bovine serum albumin at 1.4 µg/mL was put into magnetic particles, and the resulting mixture was reacted at room temperature for 30 minutes, and then was washed three times using a phosphate buffer solution having a pH of 7.2.

Then, 3.8 µL of a C-reactive protein antibody at 1.365 mg/mL was added thereto, and then the resulting mixture was reacted at room temperature for 1 hour to bind protein G to an Fc moiety of the C-reactive protein antibody. An excessive amount of the C-reactive protein antibody was washed three times with a phosphate buffer solution having pH of 7.2.

Figure 12:
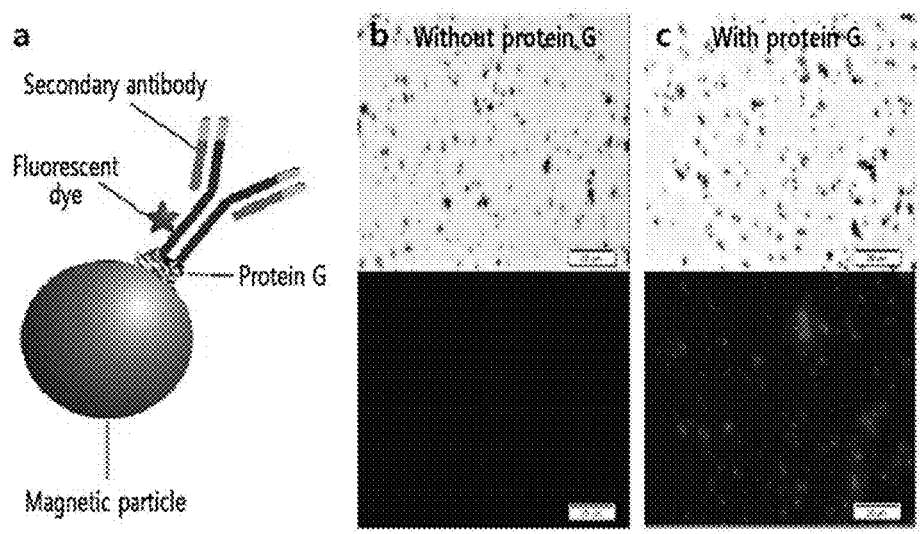
FIG. 12 is a concept view and a photograph in the case where a secondary antibody labeled with a fluorescent dye is bound to a magnetic particle according to the presence or absence of protein G in an experimental example of the present invention.

FIG. 12 illustrates a concept view and a photograph in the case where a secondary antibody labeled with a fluorescent dye is bound to a magnetic particle according to the presence and absence of protein G in order to confirm whether protein G is well fixed to the magnetic particle.

As illustrated in FIG. 12a, since protein G is specifically bound only to the Fc moiety of the antibody, the appearance of a fluorescent image means that protein G has been successfully bound only to the Fc moiety of the antibody. When there is no protein G in FIG. 12b, the bright viewing image of the magnetic particle is not overlapped with the fluorescent image of the magnetic particle. Further, when there is protein G in FIG. 12c, it can be seen that protein G has been successfully bound to the magnetic particle because the bright viewing image of the magnetic particle is overlapped with the fluorescent image.

Fixation of a C-Reactive Protein Detection Antibody to the Quantum Dot

2 µL of a protein G solution at 0.5 mg/mL was reacted with 22 µL of the C-reactive protein detection antibody at 0.035 mg/mL at room temperature for 30 minutes to bind protein G to the Fc moiety of the detection antibody. A quantum dot which had been hydrophilized by coating a lipid combination including nickel thereon was added to the previously prepared mixture, and the resulting mixture was reacted at room temperature for 1 hour. Protein G including histidine was bound to the Ni-NTA coated on the hydrophilic quantum dot to bind the C-reactive protein detection antibody to the quantum dot.

C-Reactive Protein Targeting

50 µl of a solution of magnetic particles having surfaces to which the C-reactive protein which had been previously prepared was bound was placed into 500 µl of each of the phosphate buffer solutions having pH of 7.2, which included 100 ng, 200 ng, 400 ng, 600 ng, 800 ng, and 1000 ng of C-reactive proteins, and the resulting mixture was reacted at room temperature for 1 hour. An excessive amount of the C-reactive protein was washed three times with a phosphate buffer solution having pH of 7.2 and removed. The C-reactive protein collected was sandwich-targeted by adding 352 µL of a hydrophilic quantum dot solution to which 0.2468 µM of the C-reactive detection antibody had been bound thereto. An excessive amount of the C-reactive protein detection antibody to which the quantum dot had been bound was washed with a phosphate buffer solution having pH of 7.2 and completely removed.

Figure 13:
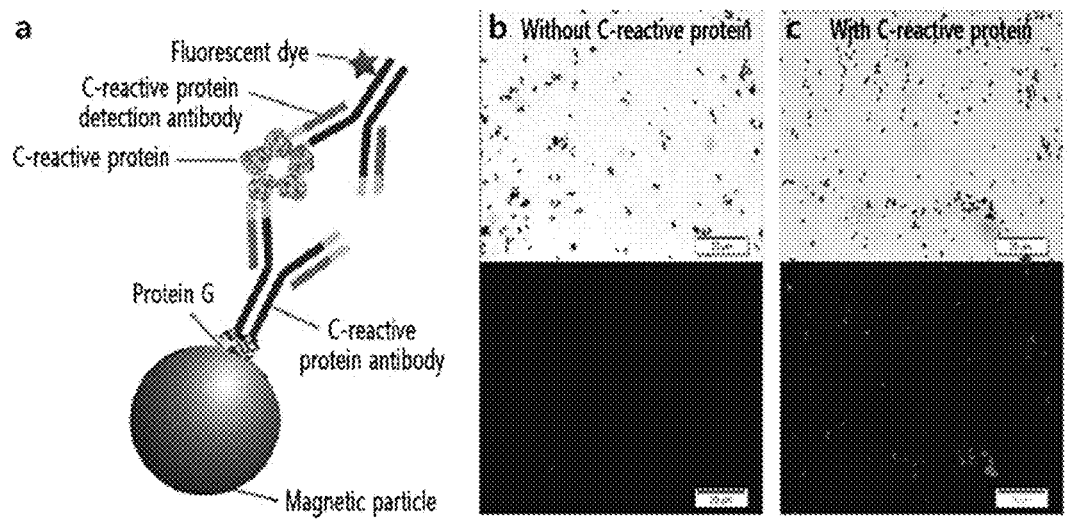
FIG. 13 is a concept view and a photograph in the case where the C-reactive protein is sandwich-targeted by the functionalized magnetic particle and a C-reactive protein detection antibody bound to a fluorescent dye according to the presence or absence of the C-reactive protein detection antibody in an experimental example of the present invention.

FIG. 13 illustrates a concept view and a photograph of the case where the C-reactive protein is sandwich-targeted by the functionalized magnetic particle and a C-reactive protein detection antibody bound to a fluorescent dye according to the presence or absence of the C-reactive protein in order to confirm whether the C-reactive protein is well sandwich-targeted.

As illustrated in FIG. 13a, since the C-reactive protein detection antibody may sandwich-target the C-reactive protein only in the case where the C-reactive protein is targeted by a C-reactive protein primary antibody, it can be seen that the C-reactive protein has been well sandwich-targeted when a fluorescent image appears. When there is no C-reactive protein in FIG. 13b, the bright viewing image was not overlapped with the fluorescent image. Meanwhile, when there is a C-reactive protein in FIG. 13 (c), it could be seen that the C-reactive protein had been well sandwich-targeted because the bright viewing image was overlapped with the fluorescent image.

Quantitative Analysis

A standard curve was prepared by measuring the absorbance of quantum dots at 0.37 nM, 0.9 nM, 1.6 nM, 3 nM, 5 nM, 12.5 nM, and 25 nM at a wavelength of 350 nm. After that, a quantum dot bound to a detection antibody of the C-reactive protein was separated by adding 100 µL of imidazole at 1M to a sandwich assay, and reacting the resulting mixture at room temperature for 30 minutes. The selectively separated quantum dots corresponding to the number of molecules of the C-reactive protein were obtained by attracting magnetic particles using a magnet, and then collecting a supernatant. A quantitative analysis was performed by measuring the absorbance of a solution obtained by the above-described method.

Figure 14:
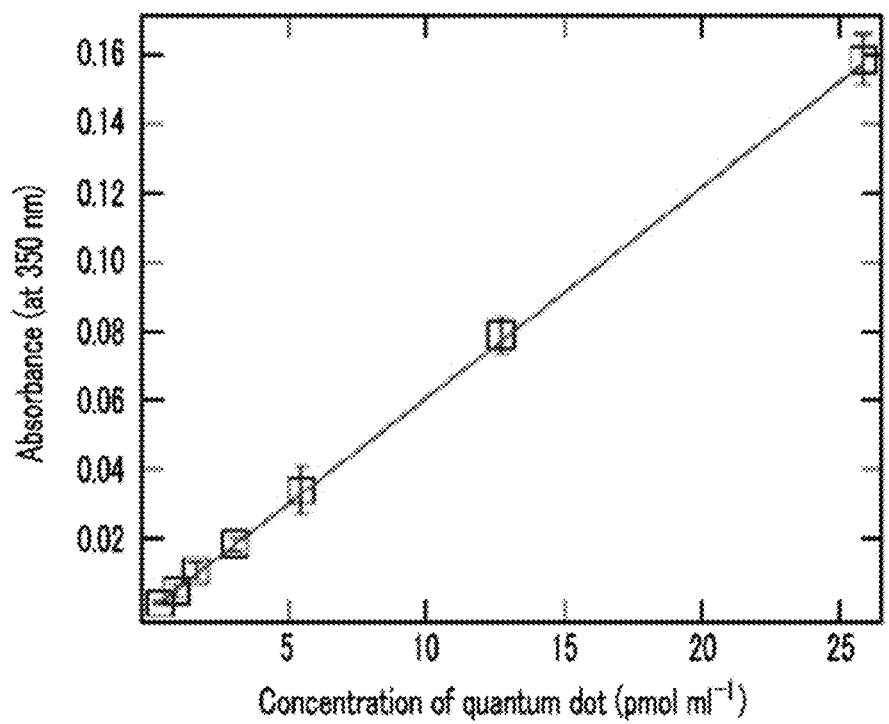
FIG. 14 is a linear graph showing the relationship between the concentration of quantum dots and absorbance through a standard curve made by using absorbance of the quantum dots at a wavelength of 350 nm in an experimental example of the present invention.

FIG. 14 illustrates a linear graph showing the relationship between the concentration of the quantum dots and the absorbance through a standard curve made by using an absorbance of the quantum dots at a wavelength of 350 nm. A concentration of quantum dots may be obtained by using a standard curve showing the relationship between the concentration of quantum dots and the absorbance illustrated in FIG. 14.

Figure 15:
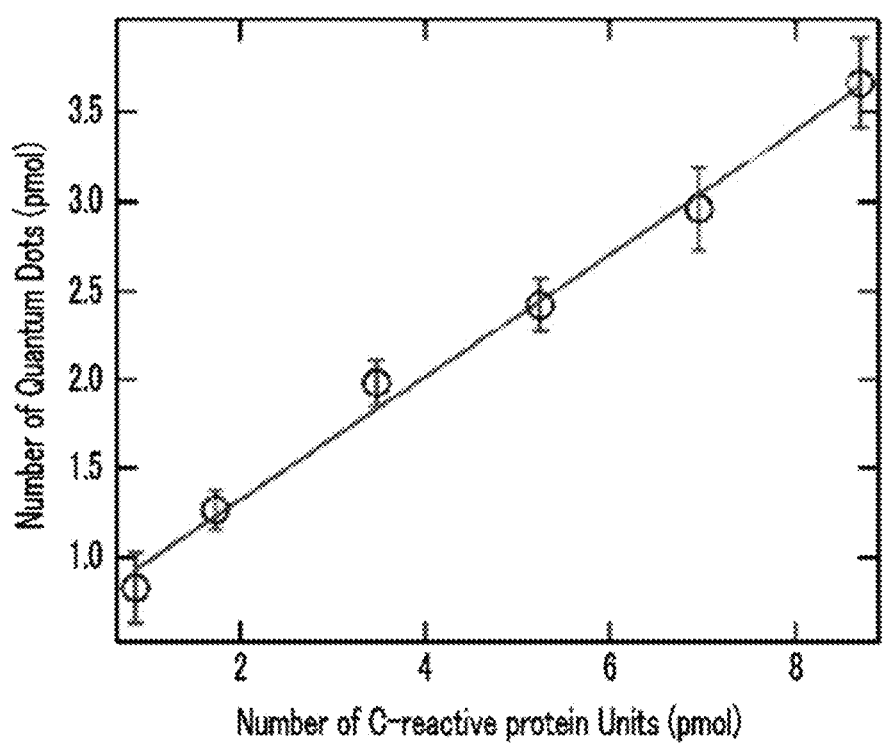
FIG. 15 is a graph quantitatively analyzing the number of C-reactive proteins through the concentration of separated quantum dots of the same number as the number of C-reactive proteins targeted in an experimental example of the present invention.

FIG. 15 illustrates a graph quantitatively analyzing the number of C-reactive proteins through the concentration of separated quantum dots of the same number as the number of C-reactive proteins targeted.

As illustrated in FIG. 15, it could be confirmed that the concentration of the C-reactive protein and the concentration of the quantum dots selectively separated from the C-reactive protein detection antibody were shown in the pmol level while the two concentrations were linearly proportional to each other.

Diagnosis Kit

A quantitative analysis was performed using optical characteristics of the quantum dot by sandwich-targeting a biomarker using a magnetic particle and a quantum dot, and selectively separating only the quantum dot bound to the biomarker detection antibody, and a quantitative analysis diagnosis kit capable of using the same was developed.

Figure 16:
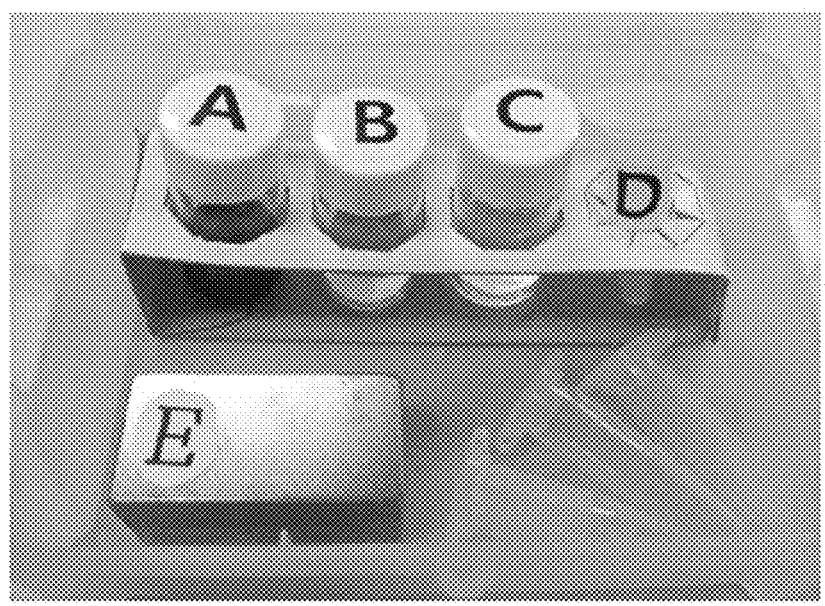
FIG. 16 and FIG. 17 are each a photograph of biomarker diagnosis kits of a first experimental example and a second experimental example of the present invention.

FIG. 16 illustrates a photograph of a biomarker diagnosis kit of the first experimental example of the present invention. The structure of the biomarker diagnosis kit in FIG. 16 is provided for illustrating the present invention, and the present invention is not limited thereto. Thus, the structure of the biomarker diagnosis kit may be modified into various forms.

As illustrated in FIG. 16, biomarker diagnosis kits were prepared into 5 constituent elements. In FIG. 16, A indicates a "magnetic particle solution for collecting a biomarker" which is functionalized by binding to an antibody for collecting a biomarker, B indicates a "quantum dot solution for quantitative analysis", C indicates a "buffer solution including imadazole", D indicates a "reaction container", and E indicates a "magnet for separating magnetic particles".

The biomarker diagnosis kit was used in the following manner. First, 100 μl of a magnetic particle solution of A was put into a reaction container of D. Then, 10 μl of serum or urine as a biomarker sample to be quantitatively diagnosed was put together into the reaction container, and the resulting mixture was reacted at room temperature for 30 minutes. Next, magnetic particles were separated by using a magnet, 100 μl of the quantum dot solution for quantitative analysis of B was added thereto, and the resulting mixture was reacted at room temperature for 30 minutes. Then, 10 μl of an imidazole buffer solution of C was added thereto, and the resulting mixture was reacted at room temperature for 30 minutes. Finally, magnetic particles were separated by bringing the magnet of E into contact with the reaction container, and then only a supernatant was put into another reaction container. Subsequently, the biomarker was quantitatively analyzed by measuring an absorbance value at 350 nm and comparing the value with a given standard curve. A disease that was indicated by the biomarker quantitatively analyzed based on a quantitative analysis result of the biomarker could therefore be diagnosed.

Experimental Example 2

A quantitative analysis was performed by simultaneously detecting multiple biomarkers. A method for functionalizing magnetic particles, a method for fixing a primary antibody to the surface of a magnetic particle, and a method for fixing a secondary antibody by hydrophilizing a quantum dot were performed in the same manner as in Experimental Example 1.

Figure 17:
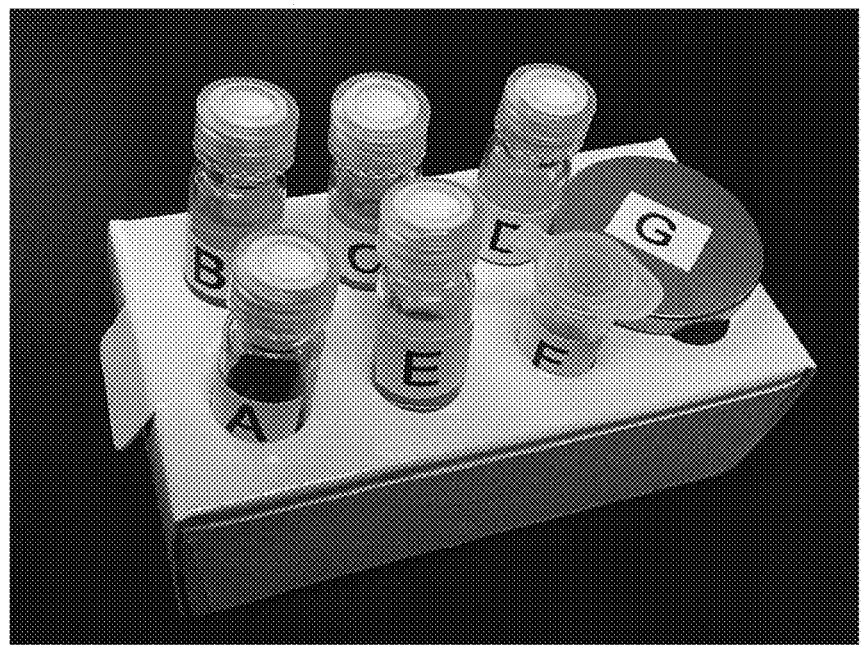

FIG. 17 illustrates a photograph of a biomarker diagnosis kit of the second experimental example of the present invention. The structure of the biomarker diagnosis kit of FIG. 17 is provided for illustrating the present invention, and the present invention is not limited thereto. Thus, the structure of the biomarker diagnosis kit may be modified into various forms.

As illustrated in FIG. 17, the A container receives magnetic particles to which a targeting antibody is bound, and the B container, the C container, and the D container receive a solution in which a detecting antibody is bound to a quantum dot exhibiting fluorescence of different colors, respectively. Further, the E container receives an imadazole solution for separating the quantum dot, F is a reaction container, and G is a magnet for separating magnetic particles. Unlike in the first experimental example, a plurality of different quantum dots are used for diagnosing multiple biomarkers in the second experimental example. Thus, the B container, the C container, and the D container are needed so that solutions in which a detecting antibody is bound to different quantum dots are used. Meanwhile, the number of the above-described containers may be modified according to the number of multiple biomarkers.

Preparation of Solutions of Group of Magnetic Particles for Multiple Detection

20 μl of an osteopontin primary antibody at a concentration of 100 μg/ml was put into 50 μl of functionalized magnetic particles and bound to the functionalized magnetic particles. Macrophage inhibitory cytokine 1 (MIC-1) and a carcinoembryonic antigen-related cell adhesion molecule 1 (ceacam1) primary antibody were also bound to the magnetic particles in the same manner as above by using the same amount of functionalized magnetic particles. 60 μl of a mixed solution of a group of primary antibody-fixed magnetic particles was prepared by mixing 20 μl of a magnetic particle solution to which the primary antibody prepared as above was bound, respectively.

Preparation of Quantum Dot Solution for Multiple Detection

Protein G was bound to an Fc moiety of the secondary antibody by reacting 3 μL of a protein G solution at 100 μg/mL with 10 μL of an osteopontin secondary antibody at 100 μg/mL at room temperature for 1 hour. Protein was also bound to a MIC-1 secondary antibody in the same manner as above by using the same amount of the protein G solution. In the meantime, the quantum dot which becomes hydrophilic by coating the lipid combination including nickel is added to the primary antibody fixed magnetic particle group mixed solution previously prepared, and then the resulting mixture is reacted at room temperature for 1 hour. In this case, the emission wavelength of the quantum dot is selected from the group consisting of approximately 520 nm, 620 nm, and 710 nm. A quantum dot exhibiting different fluorescent characteristics selected from each of the secondary antibodies targeting different biomarkers and the group of hydrophilic quantum dots.

Targeting of Multiple Biomarkers

A final volume of 400 μl of a mixed solution of a group of three different types of magnetic particles to which primary antibodies different from each other were fixed was prepared by adding a phosphate buffer solution having pH of 7.2 to 60 μl of the mixed solution of a group of three different types of magnetic particles so that three types of pancreatic cancer biomarkers (osteopontin, MIC-1, and ceacam1) have concentrations of 10 nM, 20 nM, 30 nM, 40 nM, and 50 nM, respectively. Further, the biomarkers were targeted by reacting the resulting mixtures at room temperature for 1 hour. In this case, the antibody to be used was an antibody which was selectively reacted with pancreatic cancer biomarkers that were different from each other. In the meantime, 10 μl of each of the secondary antibodies for osteopontin, MIC-1 and ceacam1 at a concentration of 100 μg/ml was bound to hydrophilic quantum dots emitting fluorescence of different colors. Osteopontin, MIC-1, and ceacam1 were then sandwich-targeted by sequentially putting different secondary antibodies into solutions targeting osteopontin, MIC-1, and ceacam1 with a mixed solution of a group of magnetic particles. The secondary antibodies to be used in this case were selectively reacted with pancreatic cancer biomarkers that were different from each other, and a quantum dot emitting fluorescence of different colors was bound to each antibody. The secondary antibodies for osteopontin, MIC-1, and ceacam1, to which an excessive amount of quantum dots have been bound were washed with a phosphate buffer solution having pH of 7.2 and completely removed.

Quantitative Analysis

Figure 18:
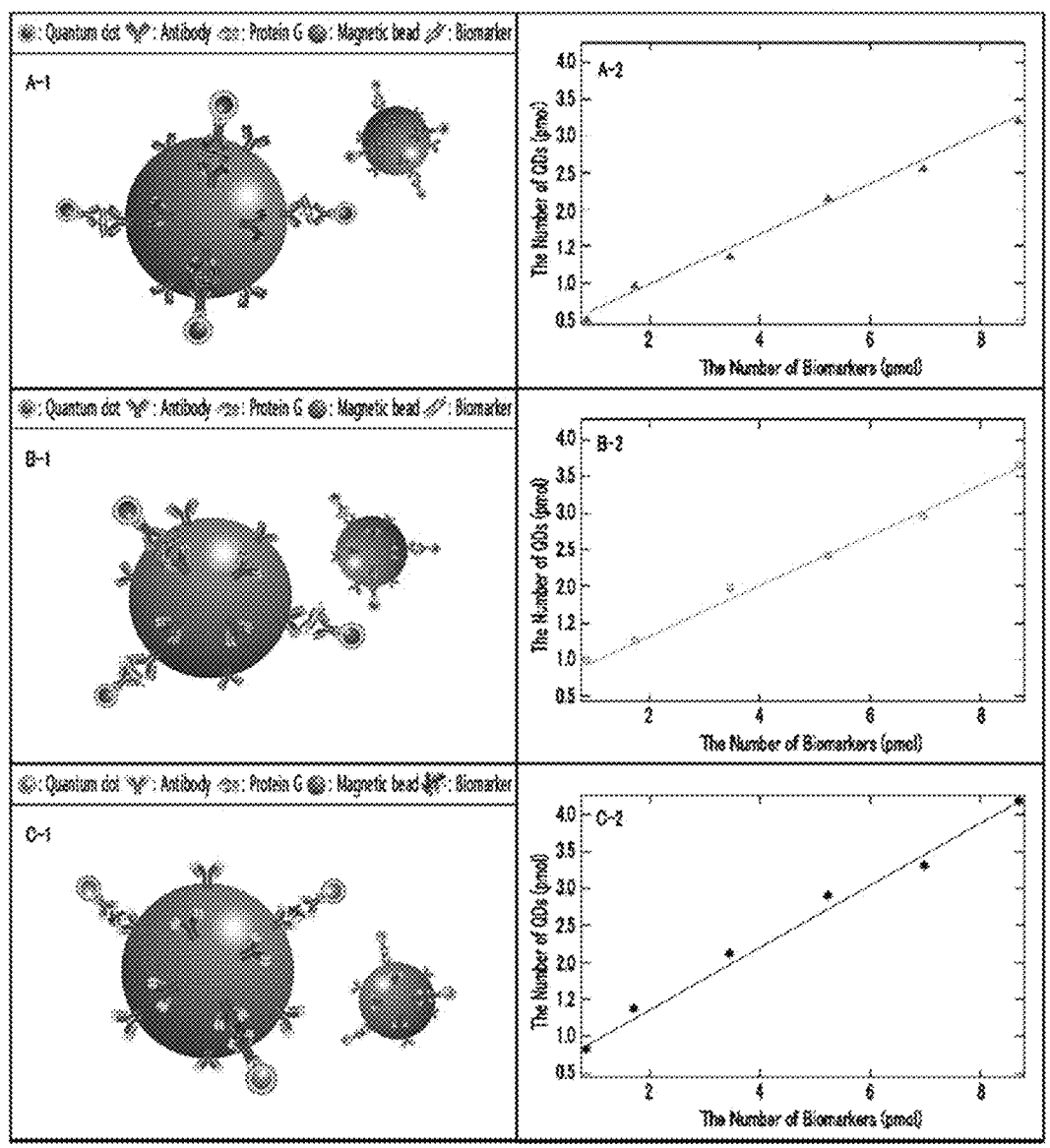
FIG. 18 shows concept views for detecting three types of biomarkers by using different quantum dots which emit wavelengths of different colors, and graphs schematically showing the detection results.

The left side of FIG. 18 shows concept views in which three different types of biomarkers are detected by using different quantum dots emitting wavelengths of different colors, and the right side of FIG. 18 shows graphs of the detection results thereof. That is, as a result of measuring a fluorescent intensity value according to each concentration using the quantum dot at concentrations of 1 nM, 2 nM, 3 nM, 4 nM, 5 nM, 10 nM, 15 nM, 20 nM, and 25 nM, the values were measured as 1385, 2755, 4202, 5611, 7452, 14,954, 23011, 32111, and 40012, and a standard curve was prepared by using the same.

Figure 19:
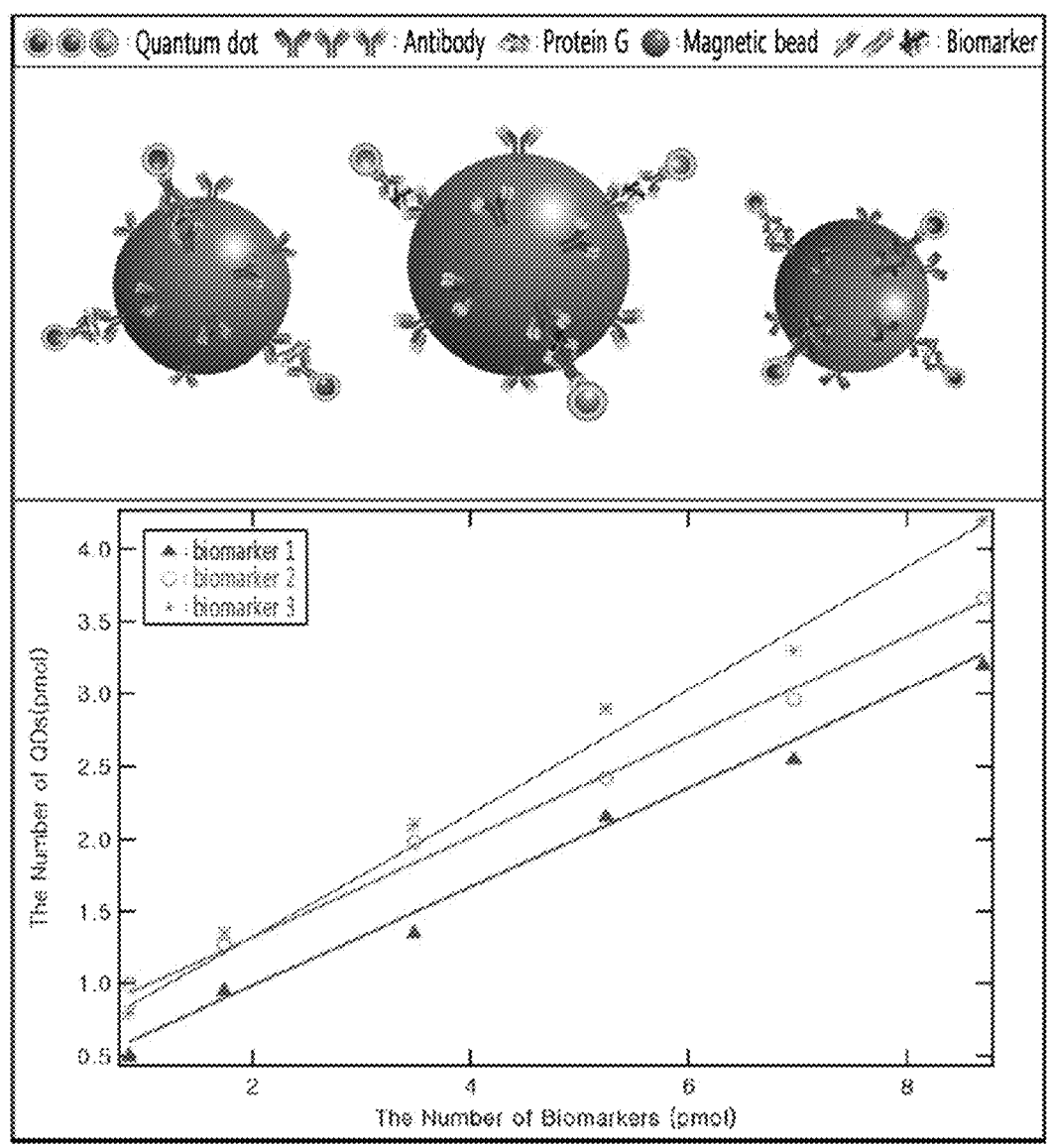
FIG. 19 shows a concept view for simultaneously detecting three types of biomarkers in FIG. 18 by using different quantum dots which emit wavelengths of different colors, and a graph schematically showing the detection results.

The upper side of FIG. 19 conceptually illustrates the process of simultaneously detecting three different types of biomarkers of FIG. 18 by using different quantum dots emitting wavelengths of different colors. Further, the lower side of FIG. 19 is a graph schematically illustrating the detection results.

Different quantum dots bound to the secondary antibodies for osteopontin, MIC-1, and ceacam1 were separated by adding 100 µL of an imidazole solution at 1M to a sandwich assay and reacting the resulting mixture at room temperature for 30 minutes. Different quantum dots corresponding to the number of osteopontin, MIC-1, and ceacam1 molecules and selectively separated were obtained by attracting magnetic particles using a magnet, and then collecting a supernatant. The fluorescent intensity value was measured so that the obtained solution had emission wavelengths of 520 nm, 620 nm, and 710 nm. Since the quantum dots used in Experimental Example 2 have emission wavelengths of 520 nm, 620 nm, and 710 nm, respectively, and do not interfere with each other, the fluorescent intensity value for each quantum dot could be obtained. Thus, it was possible to perform a quantitative analysis because the concentration of each of the separated biomarkers could be known.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

DESCRIPTION OF SYMBOLS

10. First container
20. Second container
30. Third container
40. Fourth container
50. Magnetic body
60. Description document
70. Fixing stand
80. Case
100. Biomarker diagnosis kit

What is claimed is:

1. A method for measuring a biomarker, the method comprising:

providing magnetic particles having surfaces to which a primary antibody, capable of binding a biomarker is fixed,
   wherein the providing of the magnetic particles comprises:
   functionalizing surfaces of the magnetic particles with thiol;
   binding at least one protein selected from the group consisting of protein G, protein A, protein A/G, and an Fc receptor to the thiol of the magnetic particle surfaces; and
   fixing an Fc region of the primary antibody to the protein;

providing quantum dots having surfaces to which a secondary antibody capable of detecting the biomarker is fixed through a linker protein,
   wherein the quantum dots comprise a material composed of a core/shell of CdSe/ZnS and the surfaces of the quantum dots are converted to be hydrophilic by using three lipids consisting of 1-myristoyl-2-hydroxy-sn-glycero-3phosphocholine (MHPC), 1,2-distearoyl-sn-glycero-3-phosphoethanolamine-N-(methoxy polyethylene glycol-2000) (DPPE-PEG2000), and 1,2-dioleoyl-sn-glycero-3-N-{5-amino-1-carboxypentyl}iminodiacetic acid succinyl nickel salt (Ni-NTA), and
   wherein the linker protein includes a hexahistidine sequence which is linked to the hydrophilic surface of the quantum dots through a nickel-histidine binding reaction,
   wherein the linker protein is at least one protein selected from the group consisting of protein G, protein A, protein A/G, and an Fc receptor, and
   an Fc region of the secondary antibody is fixed to the linker protein;

reacting the biomarker with the primary antibody fixed to the magnetic particles and the secondary antibody fixed to the quantum dots;

separating the magnetic particles from unbound quantum dots by using magnetic forces;

selectively separating only quantum dots bound to the magnetic particles by adding ethylenediamine tetraacetic acid (EDTA) to break a nickel-histidine binding reaction; and quantifying the concentration of the biomarker by measuring absorbance or intensity of fluorescence of the selectively separated quantum dots.

2. The method of claim 1, wherein in the binding of the linker protein, the linker protein is bound to the magnetic particle surfaces using at least one chemical linker selected from the group consisting of sulfosuccinimidyl-4-{N-maleimidomethyl}cyclohexane-1-carboxylate and succinimidyl-4-{N-maleimidomethyl}cyclohexane-1-carboxylate (SMCC).

3. The method of claim 1, wherein the quantifying of the concentration of the biomarker comprises:
   providing a plurality of solutions containing quantum dots at known concentrations;
   measuring the absorbance at a wavelength of 350 nm or the fluorescent intensity of the plurality of solutions containing quantum dots at known concentrations;
   creating a standard curve by plotting the absorbance or the fluorescent intensity of the plurality of solutions containing quantum dots at known concentrations versus the known concentrations of quantum dots;

measuring the absorbance at the wavelength of 350 nm or the fluorescent intensity of the selectively separated quantum dot;

calculating the concentration of the selectively separated quantum dot by comparing the absorbance or the fluorescent intensity of the selectively separated quantum dot with the standard curve; and quantifying the concentration of the biomarker, wherein the concentration of the biomarker is proportional to the concentration of the selectively separated quantum dot.

4. The method of claim 1, wherein the primary antibody comprises a plurality of antibodies, in the secondary antibody comprises a plurality of antibodies, and the biomarker comprises a plurality of biomarkers, wherein each biomarker in the plurality of biomarkers is different from one another, and the primary antibody and the secondary antibody for each of the biomarkers are different from each other.

* * * * *